United States Patent [19]

Tishkoff et al.

[11] Patent Number: 4,501,731
[45] Date of Patent: Feb. 26, 1985

[54] TREATMENT OF DISPARATE BLEEDING DISORDERS WITH FACTOR X ZYMOGEN

[76] Inventors: Garson H. Tishkoff, 1850 Abbott Rd., B-10, East Lansing, Mich. 48823; Douglas W. Estry, 1420 Sunnyside Rd., Lansing, Mich. 48910

[21] Appl. No.: 508,167

[22] Filed: Jun. 27, 1983

[51] Int. Cl.³ ............................................. A61K 35/16
[52] U.S. Cl. ...................................................... 424/101
[58] Field of Search .......................................... 424/101

[56] References Cited

U.S. PATENT DOCUMENTS 4,382,083  5/1983  Thomas ................................ 424/101

OTHER PUBLICATIONS

Hoffbrand et al., Recent Advances in Haematology, No. 2, (1977), pp. 431–434.
Nemerson et al., "Zymogens and Cofactors of Blood Coagulation", 1980, pp. 45–85.
DiScipio et al., Biochem., vol. 16, No. 4, (1977), pp. 698–706, "A Comparison of Human Prothrombin, Factor IX, etc.".
Esnouf, "Haemostesis", edited by Ogston & Bennett, J. Wiley & Sons, N.Y., Ch. 4, 1977, pp. 78–85.
Hilgartner et al. Blood, 61:36–40, 1983.
Liesbeth et al., New Eng. J. Med. 305:717–721, 1981.
Lusher et al., New Eng. J. Med. 303:421–425, 1980.
Prowse et al., Thrombos. Haemostas 42:1355–1367, 1979.
Aronson, Seminars in Thrombosis and Hemostatis, 6:28–43, 1979.
Menache, Thrombos. Diathes. Haemorrh., 33:600–605, 1975.
Chandra et al., Throm. Res. 12:571–582, 1978.
Barrowcliffe et al., Vox Sang. 25:426–441, 1973.
Suomela et al., Vox Sang. 32;1–16, 1977.
Subbaiah et al., Biochem. Biophys. Acta. 444:131–146, 1976.
Nesheim et al., J.B.C. 254:10952–10962, 1979.
Tishkoff, N.E.J. Med. 292:754–755, 1975.
Tishkoff, Thrombosis et Diathesis Hemorrhagica, 34:589, 1975.
Tishkoff, Published Report, pp. 103–110, (1976).
Elsinger, Published Report, pp. 77–87, 1982.
Elsinger, Published Report, pp. 1–9, World Fed. of Hemophilia, 1977.
Barrowcliffe et al., J. Lab. Clin. Med. 101:34–43, 1983.
Elsinger, Published Report, pp. 101–103, 1976.

*Primary Examiner*—Sam Rosen
*Attorney, Agent, or Firm*—Holman & Stern

[57] ABSTRACT

The invention provides a method for the treatment of disparate bleeding disorders comprising the administration of factor X zymogen in amounts sufficient to control pathological bleeding, and a therapeutic product based on the coagulant activity of a factor X zymogen-phospholipid-factor Va clotting system. The product is generally substantially free of activators for the factor X zymogen.

24 Claims, 7 Drawing Figures

TREATMENT OF DISPARATE BLEEDING DISORDERS WITH FACTOR X ZYMOGEN

BACKGROUND OF THE INVENTION

(1) Field of the Invention

The present invention relates to factor X zymogen compositions useful for inducing hemostasis. The compositions are generally substantially free of activators for the X zymogen.

(2) Prior Art

Clinical treatment of bleeding disorders arising from actual or apparent deficiencies of one or more clotting factors is commonly predicated upon a replacement therapy designed to correct the deficiency and restore the plasma concentration of the various clotting factors to that necessary to ensure adequate hemostasis.

Therapeutic materials employed in the management of bleeding disorders generally comprise plasma or plasma fractions of varying degrees of purity, typically plasma concentrates partially purified with respect to the deficient clotting factor or factors. Exemplary of such fractions are factor IX complex concentrates comprising major proportions of the vitamin K-dependent clotting factors factor II (prothrombin), factor VII, factor IX, factor X, protein C, and protein S. This concentrate, also referred to as factor IX concentrate, prothrombin complex concentrate (PCC), and prothrombin concentrate (PPSB), is used in replacement therapy for diseases associated with deficiencies of these factors, especially hemophilia B (Christmas disease), characterized by a congenital deficiency of factor IX. Surprisingly, however, factor IX concentrates, especially activated factor IX concentrates such as FEIBA and AUTOPLEX, have proved useful in the treatment of classic hemophilia with factor VIII immune inhibitor, and also in the treatment of other bleeding disorders with acquired immune inhibitors. These products also vary considerably in potency and manifestation of side effects on a clinical level. Owing to these anomalies, it has become of interest to elucidate the coagulation mechanisms involved in the therapeutic use of factor IX concentrates.

Coagulation activity of these concentrates in treating disorders other than deficiencies of the vitamin K-dependent clotting factors has been tentatively ascribed in the literature to the presence of various factors, such as factor VIII (Barrowcliffe, et al. *Thrombosis Res.* 21: 181-186, 1981), or a factor having "Xa-like activity" (Elsinger, Activated Prothrombin Complex Concentrates: Managing Hemophilia with factor VIII Inhibitor, Mariani, et al. eds. pp. 77-81, 1982). While a few parameters for the mechanism have been suggested, such as the involvement of factor V, reported results have been generally inconclusive.

OBJECTS

It is therefore an object of the present invention to provide novel factor X zymogen injectable compositions or products which provide reproducible hemostasis. It is further an object of the present invention to provide a method for the injection of the compositions. These and other objects will become apparent by reference to the following description and FIGS. 1 to 4.

BRIEF DESCRIPTION OF THE DRAWINGS

FIG. 2 presents two graphs, 2A and 2B, illustrating the effects in vitro of an inhibitor on prothrombinase activity of factors Xa and X respectively.

FIG. 4 comprises two graphs, 4A and 4B, illustrating competition in vitro for phospholipid binding sites between factors X and Xa.

SUMMARY OF THE INVENTION

The present invention relates to a method for treating mammalian deficiencies of a blood clotting protein which comprises injecting an effective amount of an injectable composition including human factor X zymogen into the blood circulatory system of the mammal, wherein the composition is substantially free of activators which convert the factor X zymogen to factor Xa. The term "substantially" means ten percent (10%) by weight or less of the activators.

The injectable compositions are generally substantially free of factors VII, VIIa, IX, IXa and Xa which are believed to activate factor X zymogen to factor Xa. The compositions preferably include factor II in a ratio to factor X of between about 1 to 10 and 10 to 1.

The invention is predicated on the identification of human factor X zymogen as an essential element in the coagulation activity of factor IX complex concentrates used in the treatment of many bleeding disorders, and the elaboration of the mechanism whereby factor X zymogen initiates blood clotting and controls hemostasis. Equally important is the recognition that other factors (VII, VIIa, IX, IXa and Xa) must be removed from the factor X zymogen compositions since they activate the X zymogen to factor Xa. Accordingly, the invention provides (1) a method for the treatment of disparate bleeding disorders comprising the injecting of factor X zymogen in amounts sufficient to control pathological bleeding, and (2) an injectable composition or product based on the coagulant activity of a factor X zymogen-phospholipid-factor Va calcium ion clotting system.

DETAILED DESCRIPTION OF THE INVENTION

Factor X zymogen is a plasma glycoprotein previously isolated and characterized (see, e.g., Esnouf, "The Biochemistry of Factor X and Factor V" "Haemostasis" edited by D. Ogston and B. Bennett, J. Wiley and Sons, New York, Chapter 4 (1977)).

The clotting activity of factor X (Stuart-Drower factor) and its deficiency disease are well recognized. According to previously accepted theory, factor X zymogen is an inactive proenzyme which, in its activated form Xa, interacts with factor Va calcium ion and phospholipid to form a prothrombin activator in both the extrinsic and intrinsic clotting systems. The complex of the enzyme Xa, calcium ion cofactor Va, and phospholipid has been designated "prothrombinase complex" in deference to its postulated function in the enzymatic conversion of prothrombin to thrombin, and it is generally accepted that this complex indeed exhibits good coagulant activity (see, e.g., Rosing, et al., J. Biol. Chem. 255: 274-283, 1980). Notwithstanding academic interest in the Xa-Va-phospholipid complex, the theory found no practical clinical application.

Research in this area has recently been extended to an in vitro exploration of coagulant activity of factor X zymogen (Tishkoff, Workshop on Inhibitors of factors VIII and IX, Vienna Facultas Verlag 103-110, 1976), which has now culminated in the discovery that factor X zymogen is itself an active catalytic species in the formation of a coagulation system comprising factor X zymogen-phospholipid-factor Va and calcium ion, and the application of this concept according to the present invention. Surprisingly it has also been found that the composition must also be substantially free of activators which convert the X zymogen to Xa. Factors which particularly can cause activation are VII, VIIa, IX, IXa and Xa. Owing to its intrinsic enzymatic activity, factor X zymogen is capable of initiating blood clotting activity by interacting with phospholipid and factor Va in the presence of calcium to form a complex capable of converting prothrombin to thrombin; providing activators are not added to increase the level of the zymogen. Other of the vitamin K-dependent clotting factors, especially factor VII, modulate the expression of factor X zymogen activity and the mechanism by which bleeding is controlled can function substantially independently of specific clotting proteins with the exception of factors II, V and fibrinogen. Thus, the X zymogen can effectively control hemostasis in diseases characterized by at least single deficiencies of clotting factors other than factors II, V and fibrinogen. Further, it is contemplated that factor X zymogen will be an exceptionally useful therapeutic material in bleeding disorders characterized by the presence of immune inhibitors, either congenital or acquired, which destroy replacement protein on transfusion. Since these immune inhibitors characteristically comprise antibodies only to deficient proteins, it is expected that administration of factor X zymogen will provide an effective therapy uncomplicated by patient immune response. The in vitro tests herein are considered reliable indicators of in vivo activity. Factor X zymogen is believed to be safe since it is already present in significant amounts in marketed mixtures of various factors.

Bleeding disorders accordingly treatable by the process of the invention include diseases characterized by congenital or acquired deficiencies of specific clotting proteins, viz, factors VIII, IX, X, XI and VII, as well as Von Willebrands' disease. The clinical management of classic hemophilia (hemophilia A) and Christmas disease (hemophilia B), and particularly these hemophilias marked by the presence of immune inhibitor, is especially contemplated. The ability to treat classic hemophilia with factor X zymogen is of major clinical importance. In addition to the inhibitor by-passing activity previously mentioned, factor X zymogen, unlike factor VIII, is a biochemically more stable glycoprotein, that may be subjected to sterilization procedures which cannot be used for factor VIII concentrates, thereby lessening the risk of transmission of disease, such as hepatitis. Further, the half-life of factor VIII in vivo is very low, about 6 hours, whereas the half-life of factor X zymogen is much higher, about 36 hours; dosage frequency can accordingly be greatly reduced in the treatment of hemophilia with factor X. Of particularly current interest is the fact that factor VIII concentrates have been tentatively linked with acquired immune deficiency syndrome (AIDS), while factor IX concentrates have not, leading to the speculation that a causal factor may exist which does not fractionate with the vitamin K-dependent factors. If this proves true, a major cause of death among hemophiliacs may be obviated by factor X zymogen therapy according to the invention.

Other bleeding disorders treatable by the administration of factor X zymogen include disorders attributable to acquired inhibitors, particularly antibodies to factors VIII, IX, XI and XII, and deficiencies of the vitamin K-dependent clotting factors resulting from hepatocellular dysfunction. Typical clinical situations are exemplified by the development of antibodies to clotting proteins in post-partum women, older patients, and patients with autoimmune disease. In addition, transient deficiencies such as those encountered during surgery may also be treated with factor X zymogen, as well as blood dyscrasias resulting from anticoagulant therapy.

Concentrates enriched in factor X zymogen of the type employed in the treatment of Stuart-Prower defect (factor X deficiency) are useful in the process of the present invention. These concentrates typically comprise factors II and X desirably purified with respect to factor X zymogen. In order to minimize risk of complications such as immune response and thromboembolic effects, it is preferable to provide a product essentially pure with respect to factor X zymogen (more than 99 percent by weight factor X zymogen). The use of a purified product further permits dose response to be monitored more readily in clinical situations. While a product comprising substantially pure factor X zymogen is most preferable, economic consideration in manufacture of the product may dictate the clinical use of plasma fractions containing residual amounts of factors II and IX, since the biochemical similarities of these proteins and factor X zymogen make separation difficult and costly and does not improve the product significantly. In general, products having a concentration of at least about 50 units per ml. of factor X zymogen, preferably between about 50 to 800 units/ml. of factor X zymogen, are broadly useful within the scope of the invention. The products should also have a high potency, with purifications of at least about 800 fold over starting plasma (as a minimum). Products purified to provide a factor X zymogen specific activity of at least about 20 units/mg. protein, and preferably, at least about 30 units/mg. protein, are suitable. Small amounts of X zymogen activators can be tolerated, but are not preferred. Most preferably, products having a factor X zymogen specific activity of at least about 120-130 units/mg protein, the approximate specific activity of pure factor X zymogen, are employed. The product preferably has minimal or no activation of the factor X zymogen to factor Xa.

The injectable compositions of the present invention include the conventional sterile buffering solutions conventionally used with factor IX concentrates. All of this is well known to those skilled in the art.

Isolation schemes such as that generally described by DiScipio, et al. (supra) are well-known; in this exemplary procedure, factor IX in a conventional DEAE-Sephadex eluate is separated from factors X, II, and protein S on benzamidine-Sepharose, followed by chromatography on the relevant eluate fractions of a poly(-homoarginine)-Sepharose column to separate factor X zymogen, in a 9,000 fold purification. It is most important, of course, that the therapeutic material not be activated to convert factor X to factor Xa.

The characterization of factor X zymogen (Esnouf, supra) suggests that the zymogen may exist in variable molecular form, e.g., single chains, double chain, monomeric, dimeric, or as aggregates of different molecular weights; carboxylated and non-carboxylated forms have also been suggested. The method of the invention includes the therapeutic use of human factor X zymogen in all its molecular forms. Factor X zymogen (human) has been historically identified as the substrate in plasma for the coagulant agent in Russell's viper venom; factor X zymogen glycoproteins which similarly function as a substrate for the coagulant agent in Russell's viper venom are herein included within the scope of the term "factor X zymogen".

Dosage of factor X zymogen will vary according to the actual therapeutic product employed, and according to disease characteristics and the severity of the condition, which may not be consistent. Broadly, sufficient zymogen is parenterally administered to induce hemostasis. A dosage sufficient to elevate blood levels of factor X zymogen to from about 50% to about 400% of normal may be required in a given clinical situation, based on observations of patients with factor VIII inhibitor treated with factor IX complex concentrate (an exemplary study is described by Kurczynski, et al., N.E.J. Med. 291:164–167, 1974). Dose response levels of essentially pure factor X zymogen may be in the range of 50 to 100% of normal.

Since factor X zymogen functions in a coagulation system with factor Va and phospholipid to convert prothrombin to thrombin, pure factor X zymogen is not useful in treating deficiencies of the required cofactor V, or factor II, unless these are supplied in conjunction with the zymogen. In deficiency diseases complicated by platelet defects, phospholipoproteins with platelet factor 3 activity may also be administered. The native phospholipids involved in prothrombin activation have not been characterized; however, the active materials are believed to have surface catalytic activity dependent upon both their chemical and physical properties.

EXAMPLES

Materials and Methods

Chromatography:

DEAE-Sephadex A-50, Sepharose 4B, QAE-Sephadex A-50, and Sephadex G-25 were the products of Pharmacia, Piscataway, N.J. Ultrogel AcA-34 was purchased from LKB Ltd., Rockville, Md. Heparin-Sepharose, benzamidine-Sepharose, poly(homoarginine)-Sepharose, RVV-X-Sepharose and AT III-Sepharose were prepared by coupling the ligand to Sepharose 4B activated with cyanogen bromide (DiScipio, et al., supra, and Downing et al., J. Biol. Chem. 25-:8897–8906, 1975).

Proteins:

Protein preparations were assessed for homogeneity by sodium dodecyl sulfate-polyacrylamide gel electrophoresis (SDS-PAGE). Protein concentrations were estimated from the absorbance at 280 nm using the following values for $E_{280}$ nm: Factor X, 1.16; prothrombin, 1.38; factor Xa, 0.96; factor V, 0.89; and AT III, 0.61 ml mg$^{-1}$cm$^{-1}$.

Factor X and prothrombin were purified from human cryosupernatant containing citrate-phosphate-dextrose-adenine (CPDA-1) as the anticoagulant (Great Lakes Regional Red Cross Blood Services, Lansing, MI.) as described by DiScipio, et al. (supra) with exception of the use of phenylmethyl-sulphonyl fluoride (PMSF) at a final concentration of $1 \times 10^{-3}$M in place of diisopropyl-fluorophosphate (DFP). The use of this binding agent may be important in the separation of the factor X zymogen. The unreduced zymogens were homogeneous by SDS-PAGE; factor X had a specific activity of 120 units/mg. The reduced factor X protein evidenced a single heavy and light chain. In addition, the NH$_2$-terminal sequence, as determined by the Protein Sequencing Laboratory, Department of Biochemistry and Biophysics, University of California, Davis, was consistent with the published data. Purified factor X was stored in 20 mM Mes-tris, pH 5.9, 2 mM benzamidine and 0.2% sodium azide at −80° C. and was dialyzed against 50 mM triethanolamine-0.2M NaCl, pH 7.4 before use. Prothrombin was stored in the same buffer and prior to use it was passed over G-25 column equilibrated in 50 mM triethanolamine-0.2M NaCl, pH 7.4.

The following is an actual Example of the preparation of the factor X zymogen.

EXAMPLE I

Five liters of cryo-poor plasma anticoagulated with CPD-A were pooled in a large plastic container. Heparin (5000 units), 1.5 mMO-phenanthroline and 250 mg of polybrene were added and the plasma was stirred for 15 minutes at 4° C. Two hundred milliliters of 1 M barium chloride was then added, with continuous stirring, over a period of 30 minutes and the plasma was stirred for an additional 15 minutes. The plasma was centrifuged at 8000 g, 4° C. for 15 minutes and the supernatant was decanted. The barium citrate pellet was then washed twice with 1 liter of 0.02 M imidazole buffer, pH 6.0, 1 mM benzamidine and 0.2 M NaCl. The pellet was then eluted by homogenizing in a siliconized glass Waring blender with 1 liter of buffer containing 0.2M Mes-HCl, pH 5.85, 0.15 M sodium citrate, 10 mM benzamidine, 1000 units of heparin and 10 mg of soybean trypsin inhibitor. The mixture was then stirred for 1 hour at 4° C. and the precipitate was removed by centrifugation at 8000 g, 4° C. for 20 minutes.

The supernatant was brought to 10% saturation with ammonium sulfate by addition of 76 g of finely ground (NH$_4$)$_2$SO$_4$, containing 1.5 ml of 1 M Tris base, over a 15 minute period and then stirred for an additional 15 minutes at 4° C. The precipitate was removed by centrifugation at 8000 g for 15 minutes at 4° C. and discarded. The supernatant was then brought to 40% saturation by the slow addition of 186 g of finely ground (NH$_4$)$_2$SO$_4$ with 9 ml of 1 M Tris base added. This precipitate was again removed and discarded and the supernatant brought to 70% saturation with 229 g of (NH$_4$)$_2$SO$_4$ containing 10 ml of 1 M Tris base. The precipitate was collected by centrifugation at 8000 g for 30 minutes and then dissolved in 50 ml of 0.02 M Tris-H$_3$PO$_4$, pH 5.85, containing 0.1 M EDTA, 2 mM benzamidine and 0.02% sodium azide. The protein was then dialyzed against 1 liter of this buffer and then against two 1 liter changes of 0.2 M Tris-H$_3$PO$_4$, pH 5.85, containing 2 mM benzamidine and 0.02% sodium azide. Dialysis was continued overnight and the fine precipitate that developed was then removed by centrifugation at 9000 g for 10 minutes.

The protein was applied to a DEAE Sephadex-A50 column (2.6×36 cm) equilibrated with 0.02 M Tris-H$_3$PO$_4$.pH 5.85, 2 mM benzamidine and 0.02% sodium azide. The column was then washed with 250 ml of the same buffer plus 0.15 M NaCl and then eluted with a linear gradient consisting of 250 ml of 0.02 M Tris-H$_3$PO$_4$, pH 5.85, 2 mM benzamidine, 0.02% sodium azide and 0.15 M NaCl and 250 ml of this buffer plus 0.55 M NaCl. The column was run at 66 ml/hour and 3.5 ml fractions were collected. The peak of protein containing the factor X activity was pooled and dialyzed against 3 one liter changes of 0.02 M Mes-tris, pH 5.9, 2 mM benzamidine and 0.02% sodium azide.

The peak of factor X activity from DEAE was applied to a benzamidine-Sepharose column (1.6×30 cm) equilibrated with 0.02 M Mes-Tris, pH 5.9, 2 mM benzamidine, 0.02% sodium azide. The column was then washed with the same buffer containing 0.3 M NaCl and the proteins were eluted with a linear gradient consisting of 250 ml of the above buffer plus 0.3 M NaCl and 250 ml of this buffer plus 1.3 M NaCl. The flow rate was 24 ml/hour and 3.5 ml fractions were collected. The factor IX and X activity were separated on this column.

The factor X activity was pooled and immediately brought to 1×10$^{-3}$ M PMSF and applied to a poly(-homoarginine)-Sepharose column (1.6×30 cm) equilibrated in 0.02 M Mes-Tris, pH 5.9, 0.02% sodium azide. The column was washed with 250 ml of 0.02 M Mes-Tris, pH 5.9, 0.02% sodium azide, 3.0 M NaCl and 2×10$^{-4}$ M PMSF. The proteins were eluted with 250 ml of 0.02 M Mes-Tris, pH 5.9, 0.02% sodium azide, 2.4 M NaCl, 2.9 M guanidine hydrochloride and 1×10$^{-3}$ M PMSF. The column was run at 16 ml/hour and 2.5 ml fractions were collected. The factor X eluting from this column was pooled and brought to 10 mM in benzamidine and then dialyzed against 1 liter of 0.02 M Mes-Tris, pH 5.9, 0.02% sodium azide, 2.4 M NaCl and 10 mM benzamidine. The factor X was then dialyzed against 2 one liter changes of 0.02M Mes-Tris, pH 5.9, 2 mM benzamidine and 0.02% sodium azide. The factor X was stored at −80° C.

Human factor Xa was prepared by the method of Downing, et al. (supra) using the factor X activating enzyme from Russell's viper venom (RVV-X) prepared according to the procedure of Kisiel et al. (Biochem. 15:4901-49906, 1976). The RVV-X was coupled to Sepharose 4B activated with cyanogen bromide. Factor X zymogen was activated by incubation with RVV-X-Sepharose in the presence of 6 mM CaCl$_2$ for 10 min. at 37° C. The reaction was stopped by addition of EDTA to a final concentration of 10 mM and the RVV-X-Sepharose was removed by filtration on a mini-column (1.4×6.5 cm.). The Xa was then dialyzed overnight against 20 mM Mes-Tris, pH 5.9, 2 mM benzamidine and 0.2% sodium azide. SDS-PAGE of factor Xa indicated that the preparation was homogeneous. The active site concentration of factor Xa was determined by titration with p-nitrophenyl-p-guanidinobenzoate (p-NPGB) according to the procedure of Smith employing an experimentally determined molar extinction coefficient for p-nitrophenol of $E_{402\ nm} = 15{,}317\ M^{-1}\ cm^{-1}$.

Factor V was isolated from fresh human plasma anticoagulated with CPDA-1 according to the method of Kane, et al. (J. Biol. Chem., 256:1002-1007, 1981). The final product had a specific activity of 75 units/mg. and showed a single high molecular weight band on SDS-PAGE. Activation of factor V was carried out in the following manner. The protein was desalted on an AcA-34 column equilibrated with 20 mM Tris-0.15M NaCl, pH 7.4 and 5 mM CaCl$_2$ to remove the benzamidine. Factor V (200 microg/ml) was incubated with alpha-thrombin (2 units/ml.) for 5 min. at 37° C. in 20 mM Tris-0.15M NaCl, pH 7.4 and 5 mM CaCl$_2$. Thrombin was removed by adsorption onto benzamidine-Sepharose followed by filtration on a mini-column to remove the gel.

Purified AT III was generously provided by Dr. M. Wickerhauser (American Red Cross, Bethesda, Md.) and contained 8.1 mg/ml of AT III and was 95% pure by SDS-PAGE.

Human fibrinogen was obtained from Kabi Group, Inc., Greenwich, Ct. A stock solution was prepared by dissolving 1.5 g in 66 ml of distilled water and then dialyzing for 12 hours against 2.4 mM sodium citrate-50 mM sodium acetate-0.15 M NaCl, pH 8.2. The protein was stored at −80° C.

Phospholipids:

Phospholipid vesicles were prepared according to the procedure of Kosow, et al. (J. Biol. Chem. 254:9448-9452, 1979), and Nelsestuen, et al. (Biochem. 16:4164-4171, 1977). A chloroform suspension, prepared by mixing 50 mg of L-alpha-phosphatidylethanolamine and 22 mg of Folch Fraction III (Sigma Chemical Co., St. Louis, Mo.), was used routinely as a source of phospholipid. After sonication and centrifugation, the phospholipid suspension was chromatographed on a Sepharose 4B column previously primed with isotonic saline extract of rabbit brain followed by thorough washing and equilibration with 20 mM triethanolamine, pH 7.4. The molar concentration of lipid in the stock solution was determined by the method of Gomori (J. Lab. Clin. Med. 27:955-960, 1942). Dilution of the stock solution were made in 50 mM triethanolamine-0.2 M NaCl, pH 7.4.

Additional Reagents:

Morpholinoethanesulfonic acid (Mes), Trizma base, guanidine hydrochloride, benzamidine, heparin sodium salt (grade 1, 164 units/mg), poly-L-lysine (M.W. 150,000-300,000), p-aminobenzamidine hydrochloride epsilon-amino-N-caproic acid, 1-cyclohexyl-3-(2-morpholinoethyl)-carbodiimide, Russell's viper venom, polyethylene glycol 6000 and p-nitrophenol were purchased from Sigma Chemical Company, St. Louis, Mo. Triethanolamine hydrochloride, 0-methylisourea hydrogen sulfate and cyanogen bromide were obtained from Aldrich Chemical Company, Milwaukee, Wi. p-NPGB was purchased from ICN Biochemicals, Cleveland, Oh. All other reagents were of the highest purity available. (p-amidinophenyl) methanesulfonyl fluoride (p-APMSF) was obtained from Dr. David Bing, Boston, Ma.

Clotting Factor and FEIBA Assay Procedures:

Prothrombin, factors X, Xa and IX were assayed by methods previously described (Biochem. Biophys. Acta, 434:199-208, 1976). Factors V and Va were assayed by a modification of the one-stage procedure of Quick (Hemorrhagic Deseases, p. 379, Lea and Febiger, Phil. 1957) where one unit of activity is defined as the amount of activity present in 1 ml of pooled normal plasma. Factor V deficient plasma, ACTIN, Factor IX deficient plasma and Activated Thromboplastin were obtained from American Dade, Miami, Fl.

FEIBA was monitored by the clot promoting activity of the test protein in the activated partial thromboplastin time (APTT) or nonactivated partial thromboplastin time (NAPTT) assay employing either factor VIII deficient plasma or factor VIII deficient plasma with an inhibitor as substrate. Inhibitor plasma was provided by Dr. John Penner, East Lansing, Michigan. Individual APTT assays were performed as follows: The test sample (0.1 ml) was added and the incubation was continued for an additional 2 minutes. Recalcification was accomplished by the addition of 0.1 ml of prewarmed 0.02 M CaCl$_2$ and the clotting time recorded. The results are expressed in seconds as the average of duplicate determinations. NAPTT assays were performed as for the APTT except rabbit brain cephalin (Sigma chemical Co., St. Louis, Mo.) was substituted for ACTIN.

Prothrombin Activation Assay:

The assay system used was a modification of the procedure of Kosow, et al.; supra, where prothrombin activation in a steady state system is monitored by the generation of thrombin; thrombin peptidase activity was assayed on the peptide anilide S-2238 (H-D-Phe-Pip-Arg-p-nitroanilide HCl, Ortho Diagnostics, Raritan, N.J.). The activation of prothrombin was carried out in disposable semimicro-cuvettes at 30° C. The reaction mixture, in total volume of 1 ml, consisted of variable concentrations of factor X (or factor Xa), prothrombin and phospholipid as specified for individual experiments. In addition, the reaction mixture contained 1 unit/ml of factor Va, 2.5 mmol/ml CaCl$_2$ and 100 micromol/ml of S-2238 in 50 mM triethanolamine-0.16 M NaCl buffer pH 7.4. The assay was performed as follow: Factor X (or Xa), factor Va, CaCl$_2$ and phospholipid were preincubated for 2 minutes. At the end of this time S-2238 was added and the endogenous rate of activation was followed for 1 minute. The reaction was initiated by the addition of prothrombin. The rate of release of p-nitroaniline was monitored by a DU spectrophotometer at 410 nm with Gilford adaptations and a chart recorder. The spectrophotometric data were fitted to the equation $A_{410\ nm} = at^2/2$ according to the procedure of Kosow, et al., supra. The slope of this line, which is directly proportional to the rate of prothrombin activation, is converted to the concentration of thrombin formed per unit time using a molar extinction coefficient for p-nitroaniline ester of 9400 and an experimentally determined first order rate constant of k=55/s for the cleavage of S-2238 by alpha-thrombin. This rate constant is in very close agreement with that determined by Kosow, et al. The endogenous rate due to spontaneous cleavage of the chromogenic substrate was subtracted from the absorbance readings prior to determination of the rate of prothrombin activation.

EXAMPLE II

The Kinetics of Prothrombin Activation

Figure 1:
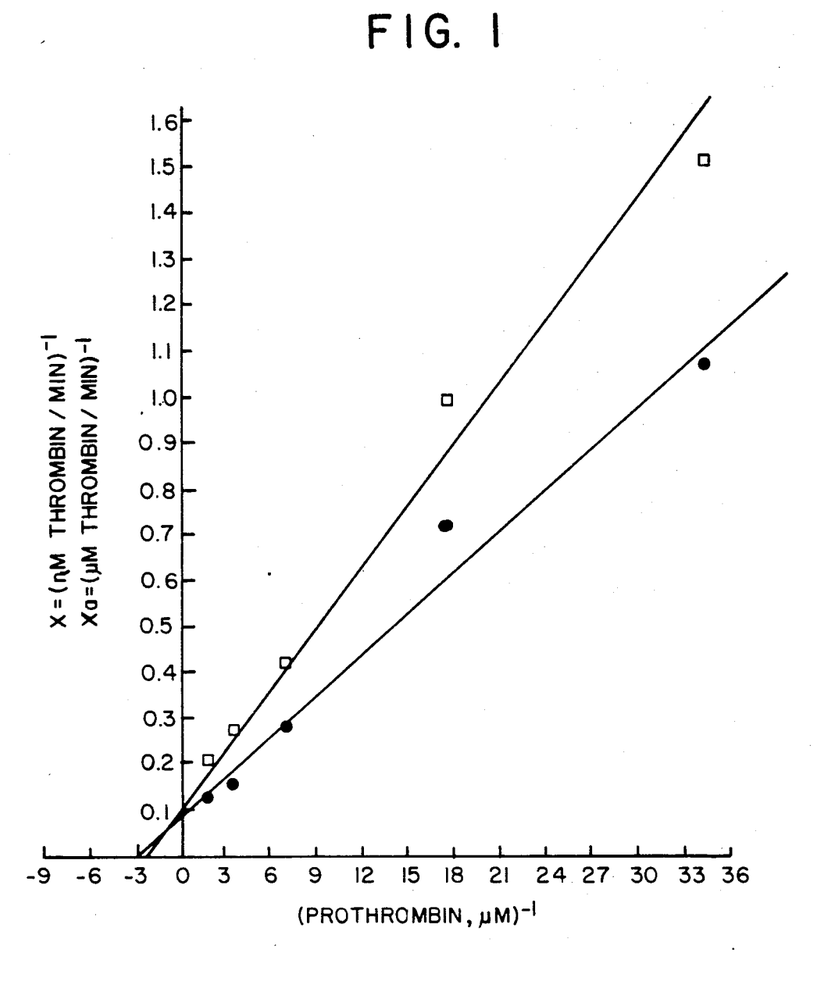
FIG. 1 is a graphical illustration of thrombin formation in vitro at various concentrations of prothrombin in the presence of factors X and Xa.

The rates of thrombin formation at various prothrombin concentrations were determined for factor Xa and factor X zymogen and the data are presented in the form of Lineweaver-burk plots (FIG. 1). The kinetic constants for the factor Xa reaction gave a $K_m$ for prothrombin of 0.28±0.19 microM and the $V_{max}$ of thrombin formation of 12.6±4.3 micromol thrombin.min$^{-1}$. The kinetic constants obtained with factor X zymogen gave a $K_m$ for prothrombin of 0.21±0.12 microM and a $V_{max}$ of thrombin formation of 11.6±3.5 micromol thrombin.min$^{-1}$. These data indicate that the proteolytic activity of native factor X zymogen is about 1000-fold less than activated factor X in the standard chromogenic assay.

EXAMPLE III

Figure 2A:
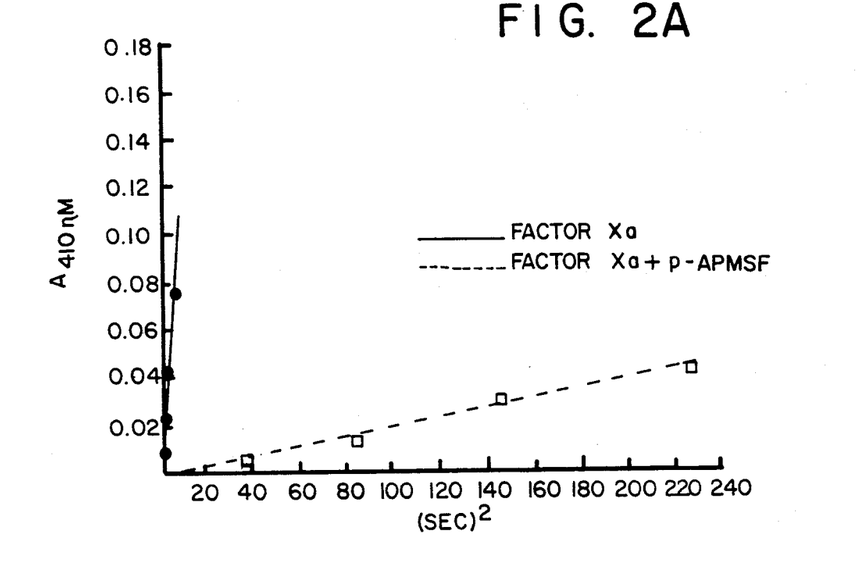
Figure 2B:
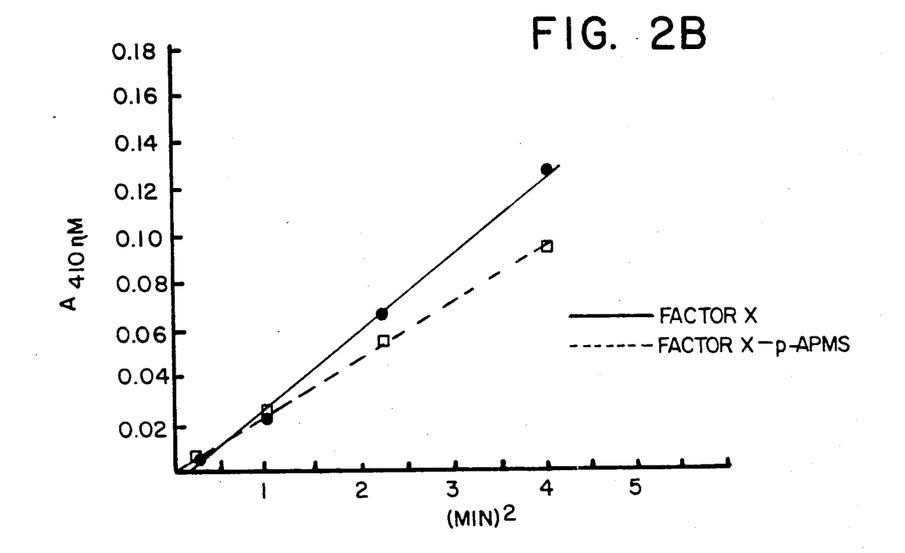
Figure 3A:
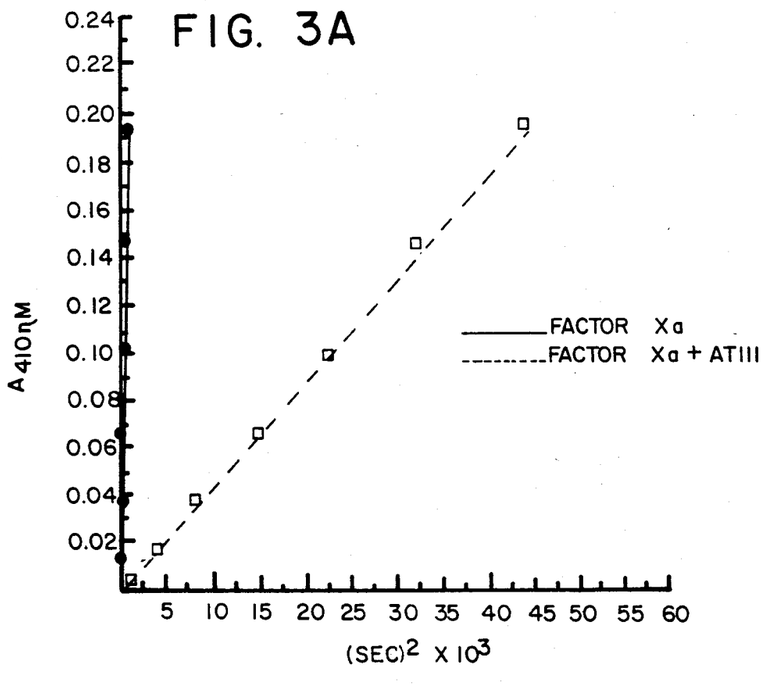
FIG. 3 is a graphical illustration of the effect of ATIII in vitro on the rate of prothrombin activation by factors X and Xa.
Figure 3B:
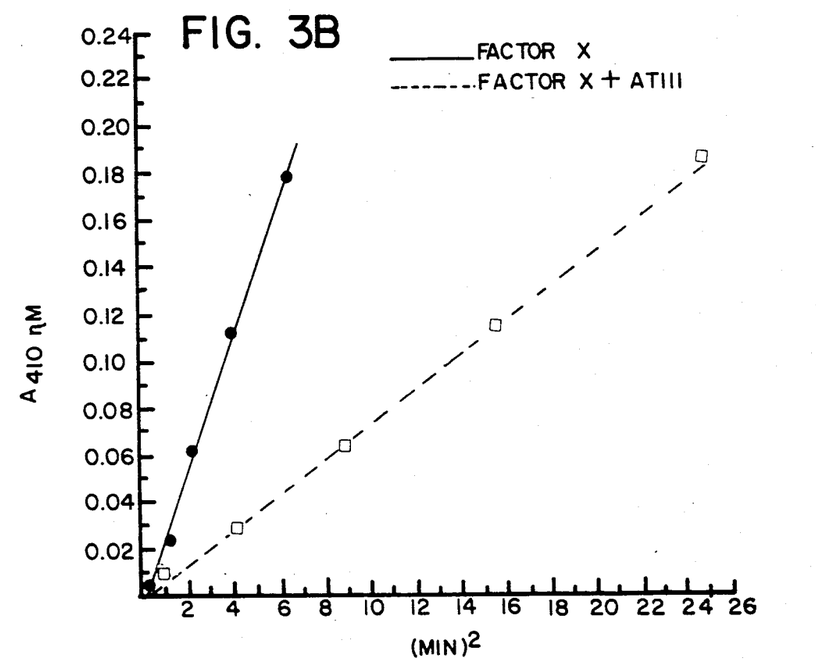

The Effect of the Inhibitor p-APMSF on the Rate of Prothrombin Activation by Factor X Zymogen or Factor Xa Experiments were carried out to ascertain whether the prothrombinase activity of factor X zymogen was due to contamination with factor Xa or was directly attributable to a slow catalytically active zymogen. The kinetics of prothrombin activation in the presence of a reactive, active site-directed inhibitor of factor Xa, p-APMSF (Laura, et al. Biochem. 19:4859–4864, 1980) were examined. After pretreatment of factor Xa with a 600-mol excess of P-APMSF, and then dialysis, inhibition of the initial reaction rate of factor Xa prothrombinase activity, expressed as change in optical density in the chromogenic assay, equivalent to approximately 95% inhibition (FIG. 2A). The same mol excess of P-APMSF evidenced virtually no inhibition of the initial reaction rate of factor X zymogen (FIG. 2B). The results obtained with p-APMSF support the hypothesis that factor X zymogen has intrinsic prothrombinase activity. It is to be noted that following pretreatment of the native zymogen with p-APMSF, there was no significant loss of procoagulant activity when the zymogen was assayed in an RVV-phospholipid activating system suggesting that the inhibitor did not bind irreversibly to the serine active site (data not shown). It is concluded from these data that the active site of activated factor X is of a different kind than the active site of the zymogen.

EXAMPLE IV

The effect of AT III on the Rate of Prothrombin Activation by Factor X Zymogen or Factor Xa Since factor Xa reacts with AT III with loss of activity, the reaction of active enzyme and zymogen with the inhibitor was compared. Experimental conditions were employed whereby the inhibitor was removed from the assay system to avoid inhibition of the thrombin product. This was accomplished by incubating factor Xa or zymogen with AT III-Sepharose, following which the residual prothrombinase activity was monitored. It is seen from FIG. 3 that both activated factor X and zymogen lost enzymatic activity in the presence of ATIII-Sepharose although the degree of activity loss by the zymogen was considerably less than that of the active enzyme. Quantitatively, the initial rates of reaction, expressed as change in optical density in the chromogenic assay, were inhibited 99% and 65% for factor Xa and zymogen, respectively. It is concluded that the zymogen is susceptible to inactivation by AT III, but the difference in rate compared with factor Xa is due to a slow-reacting active site of the zymogen.

EXAMPLE V

Figure 4A:
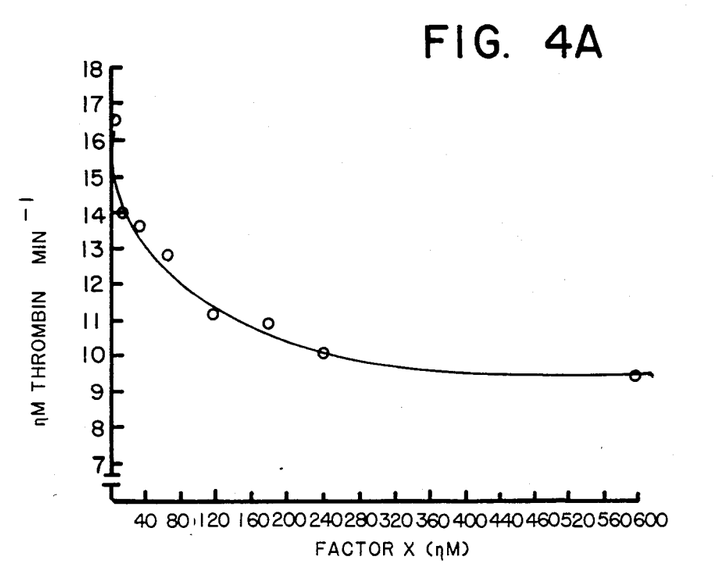
Figure 4B:
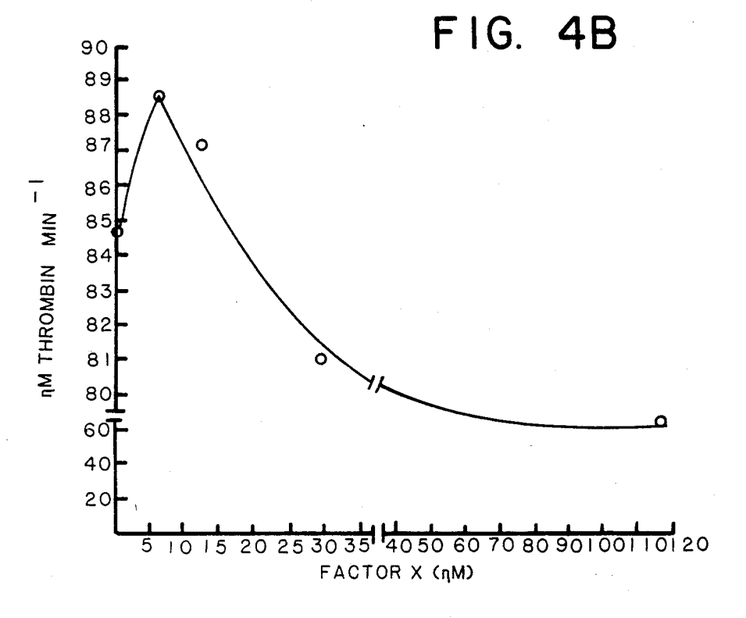

The Effects of Phospholipid Concentration on the Activity of Factor Xa in the Presence of Excess Factor X Zymogen It is accepted that the physiologic activation of prothrombin requires the interaction of clotting proteases with calcium ions, phospholipid and factor Va. It is now established that phospholipid is integral to zymogen enzymatic activity since omission of phospholipid from the reaction mixture resulted in complete loss of enzymatic activity within the limits of sensitivity of the assay (data not shown). Subbaiah, et al. (Biochem. Biophys. Acta, 444:131–146, 1976) demonstrated the ability of native factor X to bind to the same kind of phospholipid surface as prothrombin, factor Xa and factor Va. It now appears that factor X zymogen competes with factor Xa for either substrate or accessory components and that under certain conditions where both protein species are present, the binding of zymogen to cofactor would be reflected in the pattern of steady state kinetics. Zur, et al. (J. Biol. Chem. 257:5623–5631, 1982) have commented that in the combined presence of low activity zymogen and high activity enzyme, and if an obligatory cofactor (i.e. phospholipid) is rate limiting, then the zymogen would act as an inhibitor. Experiments were carried out at low and high concentrations of phospholipid at a single factor Xa concentration in the presence of varying amounts of factor X zymogen. The results are shown in FIG. 4. It is seen that with increasing concentrations of the zymogen and limiting concentrations of phospholipid, the velocity of the reaction decreases (FIG. 4A). Contrariwise, under conditions where phospholipid is increased so that the binding sites of both zymogen and enzyme are saturated, their activity should be additive and this is shown in FIG. 4B. At higher concentrations of zymogen, the phospholipid again becomes limiting, the inhibition by zymogen is again observed.

In order to determine the type of inhibition, the kinetic parameters of prothrombin activation by factor Xa under the condition where factor X zymogen is in excess, and the concentration of phospholipid is limiting, were calculated. The results summarized in Table 1 show the $K_m$ values are unchanged in the presence of zymogen but the $V_{max}$ decreased by 50%.

TABLE 1

The Effect of Factor X Zymogen on the Kinetic Parameters of the Activation of Prothrombin by Factor Xa

| Addition | $K_m$ (microM) | $V_{max}$ (nmol/min) |
| --- | --- | --- |
| None | 0.24 | 95 |
| Factor X | 0.29 | 49 |

The assays were carried out in the presence of factor Xa, 2.2 nmol/ml, factor X, 0.32 micromol/ml and phospholipid, 0.5 micromol/ml. CaCl$_2$, factor Va and S-2238 were as described under "Methods." The concentration of prothrombin was varied from 0.06 to 0.56 micromol/ml. duplicate determinations are reported.

These results suggest that factor X zymogen competes for the available phospholipid sites, and in effect lowers the concentration of the active enzyme-lipid complex. In summary, it is inferred from these experiments that the low activity zymogen can compete with the active enzyme for lipid binding sites and that factor X zymogen is an active catalytic species in the formation of the prothrombinase complex.

EXAMPLE VI

Differential Inhibition by p-APMSF and AT III of the Factor VIII Inhibitor Bypassing Activities of Factor X Zymogen and Factor Xa Additional evidence that the mechanism of human factor X zymogen activation of prothrombin is different from that of the enzyme was obtained by examination of the behavior of the zymogen in a coagulation system. These studies were directed toward demonstrating a parellelism between the steady state kinetics and a clotting assay system when the zymogen and Xa enzyme are incubated with either an organic or a macromolecular inhibitor. It is shown in Table 2 that both zymogen and factor Xa have significant FEIBA (Factor VIII inhibitor bypassing activity) in a one-stage intrinsic clotting assay and further, in the presence of a 600-mol excess of p-APMSF, a sufficient concentration to inhibit factor Xa, no inhibition of zymogen coagulant activity was observed.

TABLE 2

Differential Inhibition by p-APMSF of Factor X and Factor Xa Bypassing Activities in an Intrinsic Clotting System

| Reaction Mixture | APTT (sec) | NAPTT (sec) |
| --- | --- | --- |
| Buffer Blank | 104 | 462 |
| Factor X | 57 | 122 |
| Factor X + p-APMSF | 58 | 153 |
| Factor Xa | 27 | 44 |
| Factor Xa + p-APMSF | 84 | 291 |

Factor X zymogen and factor Xa were treated eith a 600-mol excess of p-APMSF as described in the legend to FIG. 2. 0.1 samples of factor X, 1 micromol/ml, or factor Xa, 11 nmol/ml, were assayed by APTT or NAPTT as described under "Methods" using a factor VIII inhibitor plasma (45 Bethesda units) as substrate.

Similarly, as seen in Table 3, when zymogen and enzyme were incubated with excess amounts of AT III-Sepharose and aliquots assayed for clotting activity, minimal effect was observed on zymogen coagulant activity but there was observed significant inhibition of factor Xa coagulant acitivity.

TABLE 3

Differential Inhibition by AT III-Sepharose of Factor X Zymogen and Factor Xa Bypassing Activities in an Intrinsic Clotting System

| Reaction Mixture | APTT (sec) | NAPTT (sec) |
| --- | --- | --- |
| Buffer Blank | 110 | 560 |
| Factor X | 68 | 151 |
| Factor X + AT III | 74 | 196 |
| Factor Xa | 13 | 23 |
| Factor Xa + AT III | 72 | 114 |

At zero time equal volumes of ATIII-Sepharose (9 mg/ml) and either factor Xa or factor X zymogen were incubated at 25° C. for 60 min. The ATIII-Sepharose was removed by filtration on a mini-column (1.4 × 6.5 cm). Aliquots (0.1 ml) of the filtrate were assayed as described under "Methods" by either the APTT or NAPTT using a factor VIII inhibitor plasma (45 Bethesda units) as substrate. The assay contained 3.46 nmol/ml of Xa or 0.11 micromol/ml factor X zymogen. Reactions without AT III-Sepharose were treated as described in FIG. 3.

It is considered unlikely that a serious artifact has occurred due to the presence of serine proteases contaminating the Factor X zymogen preparations that are resistant to inhibition by AT III, i.e. factor VIIa, since the system lacks its cofactor, tissue factor. These experiments provide additional support for the concept that the zymogen has intrinsic enzymatic activity and is capable of initiating blood coagulation in the presence of a spontaneous factor VIII inhibitor or inhibitors of the type known to inactivate coagulant enzymes likely to be contaminants of factor IX concentrate.

The data presented provides evidence for intrinsic prothrombinase activity of factor X zymogen, and is consistent with clinical experience with factor IX concentrates. That the activity of factor X zymogen is distinct from factor Xa activity is supported by the data showing that an active site-directed inhibitor known to iinhibit factor Xa did not signficiantly inhibit steady-state kinetics of zymogen activity (FIG. 2 and Table 2), and that the zymogen competes with factor Xa for phospholipid binding sites (FIG. 4, Table 1). The competitive binding of factor X and Xa for phospholipid may comprise an important control mechanism which initiates hemostasis in bleeding disorders. Malfunction of this control mechanism may be related to thrombogenic incidents with factor IX concentrates. While the details of factor X zymogen activity have not been completely elucidated, the therapeutic use of the zymogen will be of great clinical importance.

It will be appreciated that the factor X zymogen can be produced using recombinant genetic methods wherein genes coding for the protein are incorporated with a plasmid or vector in a microrganism. Alternatively, the protein might also be produced using hybridomas produced by fusing liver cells to a myeloma. All of these techniques are well known to those skilled in the art.

Conventionally the blood factor compositions are tested in hemophilic dogs as described in Blood vol 58, No. 5 (1981). The results of such testing will be forthcoming. This test is considered to provide a model for humans.

We claim:

1. A method for treating mammalian deficiencies of a blood clotting protein which comprises injecting an effective amount of an injectable composition including human factor X zymogen into the blood circulating system of the mammal, wherein the composition is substantially free of activators which convert the factor X zymogen to factor Xa.

2. The method of claim 1 wherein the composition includes in addition factor II.

3. The method of claim 2 wherein the weight ratio of factor X zymogen to factor II is between about 1 to 10 and 10 to 1.

4. The method of claim 1 in which the composition is substantially free of blood factors VII, VIIa, IX, IXa and Xa as activators.

5. The method of claim 1 wherein the mammal is human.

6. A method for treating mammalian deficiencies of a blood clotting protein selected from the group consisting of factor VIII, factor IX, factor XI, and factor VII comprising injecting into the mammal an effective amount of a plasma fraction including human factor X zymogen in the blood circulatory system of the mammal as an injectable composition which is essentially free of activators which convert the factor X to factor Xa and which induces reproducible hemostasis.

7. The method of claim 6, wherein factor X zymogen is present in the composition in a concentration of at least about 50 to 800 units/ml and has a specific activity of about 20 to 130 units/mg protein.

8. The method of claim 7 wherein the specific activity of factor X zymogen in the composition is at least about 120 to 130 units/mg total protein.

9. A method for treating mammalian deficiencies of a blood clotting protein selected from the group consisting of factor VIII, factor IX, factor XI, and factor VII comprising injecting an effective amount of an injectable composition including essentially pure factor X zymogen without other blood factors into the blood circulatory system of the mammal to induce hemostasis.

10. The method of Claim 9 wherein the composition additionally contains factor II.

11. The method of claim 6, wherein the mammal treated is a human.

12. A method for treating von Willebrands' disease in humans comprising injecting an effective amount of a plasma fraction of human factor X zymogen in the blood circulatory system of the mammal as an injectable composition which is essentially free of activators which convert factor X to factor Xa and which induces reproducible hemostasis in the mammal.

13. A method for treating humans with acquired inhibitors to a clotting protein selected from the group consisting of factor VIII, factor IX, factor XI, factor VII, and factor XII comprising injecting an effective amount of a plasma fraction of human factor X zymogen in the blood circulatory system of the mammal as an injectable composition which is essentially free of activators which convert the factor X zymogen to factor Xa and which induces reproducible hemostasis.

14. A method for treating bleeding disorders resulting from anticoagulant therapy with vitamin-K antagonists comprising injecting an effective amount of a plasma fraction consisting essentially of human factor X zymogen and factor II as an injectable composition in the blood circulatory system of the mammal to induce hemostasis.

15. The method of claim 14, wherein the vitamin-K-dependent clotting protein deficiency is a result of hepatocellular dysfunction.

16. An injectable composition for the treatment of blood clotting deficiencies which comprises in an injectable carrier an effective amount of factor X zymogen which is essentially free of activators which convert factor X to factor Xa.

17. The product of claim 16 in dosage unit form for administration to the mammal based upon a factor X zymogen half-life of 36 hours.

18. The product of claim 16 containing factor II and factor X and which is essentially free of factor VII, VIIa, IX, IXa and Xa as activators.

19. An injectable product for the treatment of bleeding disorders in mammals caused in whole or part by actual or apparent deficiencies of one or more clotting proteins selected from the group consisting of factors VII, VIII, IX, XI, or XII consisting essentially of an effective amount of pure human factor X zymogen alone or in admixture with factor II.

20. A method for treating mammalian deficiencies of a blood clotting protein which comprises injecting an effective amount of an injectable composition including human factor X zymogen into the blood circulating system of the mammal, wherein the composition has a specific activity of factor X zymogen of at least about 20 units per mg of protein.

21. The method of claim 20 wherein the composition includes in addition factor II.

22. The method of claim 21 wherein the weight ratio of factor X to factor II is between about 1 to 10 and 10 to 1.

23. The method of claim 20 in which the composition is substantially free of blood factors VII, VIIa, IX, IXa and Xa.

24. The method of claim 20 wherein the mammal is human.

* * * * *